United States Patent
Dertinger et al.

(10) Patent No.: US 7,410,794 B2
(45) Date of Patent: Aug. 12, 2008

(54) DEVICE BASED ON PARTIALLY OXIDIZED POROUS SILICON AND METHOD FOR ITS PRODUCTION

(75) Inventors: Stephan Dertinger, Munich (DE); Michaela Fritz, Munich (DE); Karin Fuchs, Bach (DE); Thomas Haneder, Dachau (DE); Volker Lehmann, Munich (DE); Alfred Martin, Munich (DE); Reinhard Marz, Munich (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 10/967,090

(22) Filed: Oct. 15, 2004

(65) Prior Publication Data

US 2005/0233438 A1    Oct. 20, 2005

Related U.S. Application Data

(63) Continuation of application No. PCT/EP03/03293, filed on Mar. 28, 2003.

(30) Foreign Application Priority Data

Apr. 19, 2002   (DE) ................. 102 17 569

(51) Int. Cl.
| | |
|---|---|
| G02B 6/00 | (2006.01) |
| G02B 6/10 | (2006.01) |
| G01N 33/48 | (2006.01) |
| G01N 33/53 | (2006.01) |
| G01N 21/00 | (2006.01) |
| G01N 21/76 | (2006.01) |
| G01N 15/06 | (2006.01) |
| C12Q 1/68 | (2006.01) |
| C12M 1/34 | (2006.01) |
| B01L 3/00 | (2006.01) |

(52) U.S. Cl. .............. 435/288.7; 385/12; 385/129; 385/146; 702/19; 435/6; 435/7.1; 435/287.1; 435/288.3; 436/164; 436/172; 422/99; 422/68.1

(58) Field of Classification Search ............. 385/12, 385/129, 146; 702/19; 435/6, 7.1, 287.1, 435/288.3, 164, 172, 288.7; 422/99, 68.1; 436/164, 172

See application file for complete search history.

(56) References Cited

U.S. PATENT DOCUMENTS 3,962,052 A   6/1976   Abbas et al.

(Continued)

FOREIGN PATENT DOCUMENTS

| DE | 44 26 507 A1 | 2/1996 |
|---|---|---|
| WO | WO0033976 | * 6/2000 |
| WO | WO-01/24929 A1 | 4/2001 |

OTHER PUBLICATIONS

Lehmann, V. and Foll,H. "Formation Mechanism and Properties of Electrochemically Etched Trenches in n-Type Silicon," J. Electrochem. Soc. vol. 137, No. 2, 1990.*

(Continued)

*Primary Examiner*—Long V. Le
*Assistant Examiner*—Jacqueline Diramio
(74) *Attorney, Agent, or Firm*—Dickstein Shapiro LLP

(57) ABSTRACT

Device having a flat macroporous support material made of silicon and having surfaces, a plurality of pores each having a diameter in a range of from 500 nm to 100 μm distributed over at least one surface region of the support material and extending from one surface through to the opposite surface of the support material, at least one region having one or more pores with SiO2 pore walls, and a frame of walls with a silicon core surrounding the at least one region and arranged essentially parallel to longitudinal axes of the pores and open towards the surfaces, wherein the silicon core merges into silicon dioxide over a cross section towards an outer side of the walls forming the frame.

6 Claims, 2 Drawing Sheets

U.S. PATENT DOCUMENTS

| | | | |
|---|---|---|---|
| 4,948,214 A * | 8/1990 | Hamblen | 359/654 |
| 5,544,772 A * | 8/1996 | Soave et al. | 216/2 |
| 5,843,767 A * | 12/1998 | Beattie | 435/287.1 |
| 5,874,047 A * | 2/1999 | Schoning et al. | 422/82.02 |
| 5,987,208 A | 11/1999 | Gruning et al. | |
| 7,031,566 B2 * | 4/2006 | Kochergin et al. | 385/27 |
| 2001/0045613 A1 * | 11/2001 | Nagata | 257/510 |
| 2002/0191884 A1 | 12/2002 | Letant et al. | |
| 2004/0175710 A1 * | 9/2004 | Haushalter | 435/6 |
| 2005/0054084 A1 * | 3/2005 | Lehmann | 435/6 |
| 2005/0112652 A1 * | 5/2005 | Dertinger et al. | 435/6 |

OTHER PUBLICATIONS

U.S. Appl. No. 10/678,757, filed Oct. 2003, Dertinger et al.*

G. Masini et al.; "Si based optoelectronics for communications"; Materials Science and Engineering B, Elsevier Sequoia, Lausanne, Switzerland, vol. 89, No. 1-3, Feb. 14, 2002, pp. 2-9.

A. Birner et al.; "Silicon-Based Photonic Crystals"; Advanced Materials, Wiley-VCH Verlag GmbH, Adv. Mater 2001, vol. 13, No. 6, Mar. 16, 2001, pp. 377-388.

* cited by examiner

DEVICE BASED ON PARTIALLY OXIDIZED POROUS SILICON AND METHOD FOR ITS PRODUCTION

CROSS-REFERENCE TO RELATED APPLICATION

This application is a continuation of International Patent Application Serial No. PCT/EP03/03293, filed Mar. 28, 2003, which published in German on Oct. 30, 2003 as WO 03/089925, and is incorporated herein by reference in its entirety.

FIELD OF THE INVENTION

The present invention relates to a device comprising a flatly designed macroporous support material based on silicon, which has a multiplicity of pores with a diameter in the range of from 500 nm to 100 μm distributed over at least one surface region and extending from one surface through to the opposite surface of the support material, wherein the device has at least one region which comprises one or more pores with $SiO_2$ pore walls, and wherein this region is surrounded by a frame of walls with a silicon core which is arranged essentially parallel to the longitudinal axes of the pores and is open towards the surfaces, wherein the silicon core merges into silicon dioxide over the cross section towards the outer side of the walls forming the frame. The device according to the invention is a suitable basis for a "biochip base module" in methods for detecting biochemical (binding) reactions and, in this context, in particular for the study of enzymatic reactions, nucleic acid hybridizations, protein-protein interactions and other binding reactions in the field of genome, proteome or active-agent research in biology and medicine.

BACKGROUND OF THE INVENTION

In molecular biology, increasing use is being made of biochips with which discoveries about organisms and tissue can be made in a rapid fashion. The detection of (bio)chemical reactions, that is to say the detection of biologically relevant molecules in a defined study material, is extremely important for the biosciences and medical diagnosis. In this scope, the development of so-called biochips is being constantly pursued. Such biochips are usually miniaturized hybrid functional elements with biological and technical components, in particular biomolecules which are immobilized on a surface of a biochip base module and are used as specific interaction partners. The structure of these functional elements often has rows and columns. The term "microarrays" is then used. Since thousands of biological or biochemical functional elements can be arranged on one chip, they generally need to be fabricated using microtechnological methods.

Particularly suitable as biological and biochemical functional elements are: DNA, RNA, PNA, (in the case of nucleic acids and chemical derivatives thereof, there may for example be single strands, triplex structures or combination thereof present), saccharides, peptides, proteins (for example antibodies, antigens, receptors), derivatives from combinatorial chemistry (for example organic molecules), cell components (for example organelles), cells, multicellular organisms, or cell groups.

So-called microarrays are the most widespread variant of biochips. They are small wafers ("chips") for example of glass, gold, plastic or silicon. In order to detect corresponding biological or biochemical (binding) reactions, for example, small amounts of various solubilized capture molecules, for example a known nucleic acid sequence, are fixed on the surface of the biochip base module in the form of very small droplets, so-called dots, in a point-like and matrix-like fashion.

In practice, a few hundred to a few thousand droplets are used per chip. An analyte to be studied, which may for example contain fluorescence-labelled target molecules, is then pumped over this surface. This generally leads to various chemical (binding) reactions between the target molecules contained in the analyte and the fixed or immobilized capture molecules. As mentioned above, the target molecules are labelled with dyestuff molecule components, usually fluorochromes, in order to observe these reactions or bindings. The presence and the intensity of light which is emitted by the fluorochromes provides information about the progress of the reaction or binding in the individual droplets on the substrate, so that conclusions can be drawn about the presence and/or the property of the target molecules and/or capture molecules. When the corresponding fluorescence-labelled target molecules of the analyte react with or bind to the capture molecules immobilized on the surface of the support substrate, this reaction or binding can be detected by optical excitation with a laser and measurement of the corresponding fluorescence signal.

Substrates with a high but defined porosity have many advantages over planar substrates as a basis for such biochips. More detection reactions can take place on the greatly enlarged surface area. This increases the detection sensitivity for biological assays. When the target molecules dissolved in the analyte are pumped through the channels between the front and back sides of the porous substrate, they are brought in close spatial contact with the surface of the substrate (<10 μm). On this size scale, diffusion is a very effective transport process which quickly covers the distance between a target molecule to be detected and the capture molecules immobilized on the surface. The rate of the binding reaction can thereby be increased so that the duration of the detection method can be significantly shortened.

Electrochemically produced porous silicon is an example of a substrate with such a defined porosity (cf. DE 42 02 454 A1, EP 0 553 465 A1 or DE 198 20 756 A1).

Many of the analytical methods currently used in active-agent research and clinical diagnosis employ optical methods for the detection of binding events between a substance to be detected and capture molecules (for example DNA hybridizations, antigen-antigen interactions and protein interactions). The substance to be detected is in this case provided with a marker which fluoresces after excitation with light of a suitable wavelength (fluorescence method) or which initiates a chemical reaction that in turn produces light (chemiluminescence method).

When the substance to be detected, that is to say the target molecule, binds with the immobilized capture molecule on the surface, then this can be detected optically, for example by means of luminescence. The term "luminescence," is in this case intended to mean the spontaneous emission of photons in the ultraviolet to infrared spectral range. The luminescent excitation mechanisms may be optical or non-optical in nature, for example electrical, chemical, biochemical and/or thermal excitation processes. Therefore, in particular, chemi-, bio- and electro-luminescence as well as fluorescence and phosphorescence are intended to be covered by the term "luminescence," in the scope of this invention.

Porous substrates with a high optical density and low reflectivity, for example porous silicon whose reflectivity is 50 to 70% in the visible range of the spectrum, however, do not give the expected results in conjunction with fluorescence or chemiluminescence methods in so far as the experimentally observed light-signal yield falls far short of the theoretically achievable values. The reasons for reduced experimentally determined light-signal yields compared with the theoretical values when such porous substrates are used are, on the one hand, problems with emitting the fluorescence of the substance or binding to be studied, and on the other hand—when a fluorescence method is used—problems with the optically exciting the fluorescence.

If (luminescent) light is produced throughout the volume of the pores, then the reflectivity of the pore walls is a crucial factor with a view to effective delivery of the optical signal to the surface. In the case of chemiluminescence, the light signal is radiated isotropically in all directions of space. Consequently, only a very small proportion of the generated light radiates directly in the aperture angle of the individual pore. All other optical paths are reflected several times by the walls of the pores before they reach the opening of the pore in question. Even with reflectivities which are only a little less than 100%, however, the intensity of a signal will be greatly reduced after multiple reflections. This means that this proportion of the generated signal will be greatly attenuated on its way out of the pore, and can then scarcely make any contribution to the overall signal.

Attenuation due to multiple reflections by the pore walls, which has already been described in connection with the problems of exciting the fluorescence, furthermore constitutes a serious problem for emitting the luminescence. Only fluorophors (fluorescent substances in the analyte) which radiate directly towards the pore opening are available unattenuated for a fluorescence signal. All the other optical paths are reflected at least once by the walls of the pores before they reach the opening of the pore. Even with reflectivities which are only a little less than 100%, these multiple reflections will lead to a significant attenuation of the optical signal to be detected.

In order to resolve the aforementioned problems of intensity attenuation due to multiple reflections, it has been proposed to arrange reflection layers on the pore walls in order to reduce the reflection losses, so that the excitation and emission light can be delivered better from the pores. But this solution approach does not lead to any significant improvement of the signal yield.

SUMMARY OF THE INVENTION

It is therefore an object of the present invention to provide a device or "biochip base module" for the detection of biochemical reactions and/or bindings which, in the scope of analysis methods based on fluorescence or chemiluminescence, is intended to deliver a high absolute signal yield with an improved signal-to-noise ratio, so as to increase the detection sensitivity of tests to be carried out with the final biochip.

In particular, a device is provided which comprises a flatly-designed macroporous support material 10 based on silicon, which has a multiplicity of periodically arranged discrete pores 11 with a diameter in the range of from 500 nm to 100 µm distributed over at least one surface region and extending from one surface 10A through to the opposite surface 10B of the support material, wherein the device has at least one region 11A which comprises one or more pores with $SiO_2$ pore walls, and wherein this region is surrounded by a frame 12 of walls with a silicon core 12A which is arranged essentially parallel to the longitudinal axes of the pores and is open towards the surfaces 10A, 10B, wherein the silicon core merges into silicon dioxide over the cross section towards the outer side of the walls forming the frame.

The device according to the invention has $SiO_2$ regions which are locally oxidized fully, that is to say regions which comprise one or more pores with $SiO_2$ pore walls. These fully oxidized regions are in turn surrounded by a superstructure. The fully oxidized regions are framed or surrounded by walls made essentially of silicon, so that these walls made essentially of silicon form a frame or cylinder which is open towards the surfaces 10A, 10B, whose cylinder axis extends parallel to the pores and which surrounds or encloses the $SiO_2$ regions which are locally oxidized fully. The walls forming the frame have a silicon core, and, as viewed over a cross section extending in the surface plane of the support material, the silicon core merges into silicon dioxide over the cross section towards the outer side of the walls. The frame or superstructure may have any desired configuration. According to the present invention, the frame 12 may also be open as sub-frames on one or more sides, that is to say one or more of the walls forming the frame is absent.

In the fully oxidized regions, the walls between the pores are made entirely of $SiO_2$. These regions are therefore transparent for wavelengths especially in the visible range. The device according to the invention therefore has locally transparent $SiO_2$ regions, and these transparent regions are in turn surrounded by a reflective frame of walls with a silicon core. In other words there are locally fully transparent $SiO_2$ regions, which are separated from one another by non-transparent walls with a silicon core that substantially form a secondary structure in the device according to the invention.

The frame 12 of walls with a silicon core, which merges into silicon dioxide towards each of the two outer sides, eliminates scattered light and optical crosstalk between the regions which comprise one or more pores with $SiO_2$ pore walls. This is a substantial advantage over porous substrates which are fully transparent (for example $SiO_2$, glass chips or $Al_2O_3$).

In the device according to the invention a multiplicity of pores, usually arranged periodically, are arranged distributed over at least one surface region of the flatly designed macroporous support material 10 and extend from one surface 10A to the opposite surface 10B of the support material. Blind holes, that is to say pores which are open only towards one of the surface sides 10A, 10B, may also be locally provided on the flatly designed macroporous support material 10 in the scope of the present invention.

The macroporous support material which is used has a pore diameter of from 500 nm to 100 µm, preferably from 2 to 10 µm. The thickness of the macroporous support material is usually from 100 to 5000 µm, preferably from 300 to 600 µm. The spacing from pore centre to the pore centre (pitch), that is to say of two mutually neighbouring or adjacent pores, is usually from 1 to 500 µm, preferably from 3 to 100 µm. The pore density is usually in the range of from $10^4$ to $10^8/cm^2$.

The pores 11 in the device according to the invention may, for example, be configured essentially round or elliptically. In a preferred embodiment of the present invention, the pores 11 with $SiO_2$ pore walls are designed essentially squarely. The frame 12 of walls with a silicon core 12A may then be in an essentially square or rectangular shape.

The present invention also relates to a method for the production of a device according to the invention as described above, comprising the following steps:

(a) preparing a support material made of silicon with the surfaces 10A, 10B;

(b) producing blind holes whose depth is less than the thickness of the support material by electrochemical etching into one surface 10A of the support material, in such a way that the spacing of the blind holes provided in an otherwise essentially regular arrangement is locally modified to form inter-region transitions with an increased silicon wall thickness, wherein the thickness of the silicon walls between the inter-region transitions is configured to be greater than the thickness of the silicon walls inside the region by the amount of the increased blind-hole spacing;

(c) at least locally arranging a mask layer on the surface 10A and the surface of the blind holes produced in step (b);

(d) eroding the support material at least as far as the bottom of the blind holes in order to obtain pores 11 which extend from one surface 10A through to the opposite surface 10B of the support material;

(e) removing the mask layer; and (f) subjecting the support material obtained in step (e) to a thermal oxidation so that, as a function of the silicon wall thickness, the regions with thinner silicon walls are fully oxidized whereas the silicon walls are not fully oxidized in the inter-region transitions with an increased wall thickness, so that a silicon core is left remaining in the walls.

The silicon support material prepared in step (a) may, for example, be n-doped monocrystalline silicon (Si wafer).

In step (b) of the method according to the invention, electrochemical etching is then carried out in the silicon. Such a method is known, for example, from EP 0 296 348, EP 0 645 621, WO 99/25026, DE 42 02 454, EP 0 553 465 or DE 198 20 756, to which reference is made in full scope and the disclosure of which is therefore intended to be part of the present invention. In the scope of such electrochemical etching, blind holes or pores with an aspect ratio of for example 1 to 300 or more may be etched in an essentially regular arrangement in silicon. Since, with suitably selected parameters, the electrochemical pore-etching method makes it possible to alter the pore spacing (pitch) within particular limits, the thickness of the resulting silicon walls can be locally varied by changing the pore spacing or omitting an entire row of pores in the otherwise regular arrangement of blind holes or pores.

In order to obtain pores which pass through the support material or substrate (Si wafer) and are open on both surfaces 10A, 10B, silicon is eroded on the rear side of the Si wafer in steps (c), (d) and (e), for example by KOH etching, after having etched the blind holes, whereas the front side of the wafer and the inside of the blind holes or pores are protected by a mask layer, for example a silicon nitride layer produced by CVD deposition with a thickness of, for example, 100 nm. The mask layer may then be removed in step (e), for example by means of an HF treatment. Sputtering, laser ablation and/or polishing processes, for example a CMP process, are likewise suitable for the rear-side erosion of the Si wafer.

This produces a silicon wafer or silicon support material which is matricially provided with regular pores, the pores constituting through-tubes which connect the front and rear side of the wafer together.

The diameter of these pores may be enlarged or widened after their production, for example by etching in KOH. If Si(100) is used as a starting material, then essentially square pores are obtained by such etching owing to the crystal structure. For example, assuming a pore diameter of about 5 µm with a spacing of 12 µm between the mid-points of two pores (pitch) then, for example, the pore diameter can in this way be enlarged from 5 µm to 10 or 11 µm. The thickness of the silicon walls between the pores is increased to 2 or 1 µm at the same time. A square lattice of thin silicon walls is substantially obtained in this way. The depth of the pores, or the length of the silicon walls, in this case corresponds to the original thickness of the silicon wafer less the thickness of the Si layer eroded when opening the pores on the rear side.

In step (f), the lattice obtained in this way is converted into $SiO_2$ in a thermal oxidation process, for example at a temperature of 1100° C. and with a duration of 6 hours, by oxidation as a function of the pore-wall thickness in question. The structure of the substrate is essentially unchanged by this, apart from a volume increase of the wall regions due to the oxidation of Si to $SiO_2$.

If the mutual spacing of the blind holes or pores is increased periodically in step (b), for example every 5, 10 or 20 pores, for example by 1 µm, then this provides a superstructure which is composed of regions with arrays of pores (for example 5×5, 10×10, 20×20). The thickness of the silicon walls between these regions is greater than the thickness of the silicon walls inside the regions by the amount of the increased pore spacing.

The regions with thin silicon walls will be fully oxidized to $SiO_2$ during the subsequent oxidation in step (f). But in the transitions between the regions, which have an increased wall thickness, the silicon walls are not completely oxidized so that a silicon core is left remaining in the walls, with the silicon core respectively merging into silicon dioxide over the cross section towards the outer side of the walls forming the frame. This provides locally completely fully transparent regions of $SiO_2$, which are separated from one another by non-transparent walls with the silicon core.

The application or binding of linker molecules may be carried out immediately after this. Such a linker molecules are not subject to any specific restriction, so long as they are capable of covalently binding to the OH groups present on the surface of the $SiO_2$ layer and furthermore have a functional group which is capable of covalently binding with capture molecules that can be used as probes in biological-chemical reactions. Such linker molecules are usually based on a silicon-organic compound. Such bifunctional silicon-organic compounds may, for example, be alkoxysilane compounds having one or more terminal functional groups selected from epoxy, glycidyl, chloro, mercapto or amino. The alkoxysilane compound is preferably a glycidoxyalkylalkoxysilane, for example 3-glycidoxypropyltrimethoxysilane, or an aminoalkylalkoxysilane, for example N-β-(aminoethyl) γ-aminopropyltrimethoxysilane. The length of the alkylene residue acting as a spacer between the functional group, for example epoxy or glycidoxy, which binds with the capture molecule or the probe, and the trialkoxysilane group is not subject to any restriction in this case. Such spacers may also be polyethylene glycol residues.

To complete the preparation of a biochip, capture molecules such as oligonucleotides or DNA molecules may then be bound or coupled to the support material via the linker molecules according to the standard methods of the prior art, for example by treating the porous substrate material, when epoxysilanes are used as linker molecules, by subsequent reaction of the terminal epoxide groups with terminal primary amino groups or thiol groups of oligonucleotides or DNA molecules which, in corresponding analysis methods, function as immobilized or fixed capture molecules for the target molecules present in the analyte to be studied. The oligonucleotides which can be used as capture molecules may, for example, in this case be prepared by using the synthesis strategy as described in Tet. Let. 22, 1981, pages 1859 to 1862. During the production method, the oligonucleotides may in this case be derivativized with terminal amino groups at either the 5 or 3 end position. Another way of binding such capture molecules to the inner-wall surfaces of the pores may be carried out by first treating the substrate with a chlorine source, for example $Cl_2$, $SOCl_2$, $COCl_2$ or $(COCl)_2$, optionally by using a radical initiator such as peroxides, azo compounds or Bu₃SnH and subsequently reacting it with a corresponding nucleophilic compound, in particular with oligonucleotides or DNA molecules which have terminal primary amino or thiol groups (see WO 00/33976).

The device according to the invention may fulfil the function of a 96-sample support with the density of a microarray. Microchip technologies available in the prior art can furthermore be parallelized on the basis of the device according to the invention.

The device according to the invention is also suitable in particular for the locally limited, light-controlled synthesis of molecules on the pore walls. The present invention therefore also relates to a method for controlling chemical or biochemical reactions or syntheses, comprising the following steps:
preparing a device or biochip according to the invention;
introducing a synthesis substance into at least one of the pores of the support material; and
shining light into the pores in order to optically excite at least the synthesis substance.

For planar substrates, the method of light-controlled synthesis is described, for example, in EP 0 619 321 and EP 0 476 014. Full reference is made to the disclosure of these documents in respect of the structure and light-controlled synthesis method so that, to this extent, these documents also form part to the disclosure of the present application. By propagating the light efficiently into the pores, it is possible to drive or control photochemical reactions on the pore walls. In particular, way complex sequential light-controlled photochemical reactions can in this be carried out on the pore boundary surfaces.

Optical crosstalk between the individual pores or regions/compartments is prevented by the reflective walls made essentially of silicon. The source a major problem with light-controlled synthesis on planar substrates.

BRIEF DESCRIPTION OF THE DRAWINGS

The present invention will be described by way of example below with reference to the figures, in which.

DETAILED DESCRIPTION OF THE PREFERRED MODE OF THE INVENTION

Figure 1A:
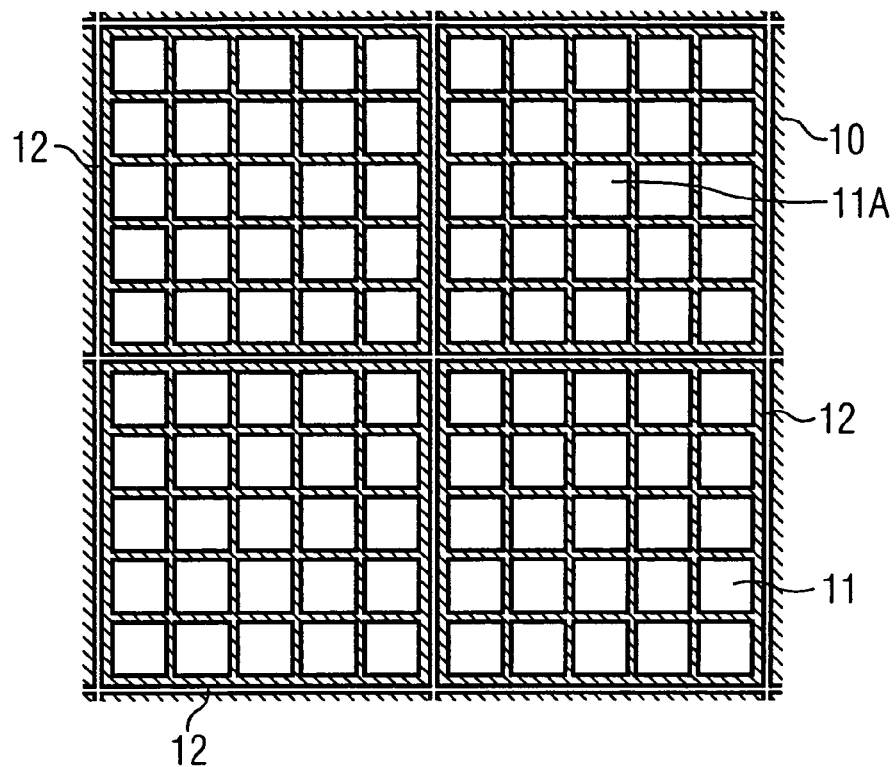
FIG. 1A shows a schematic plan view of an embodiment of a device according to the invention.
Figure 1B:
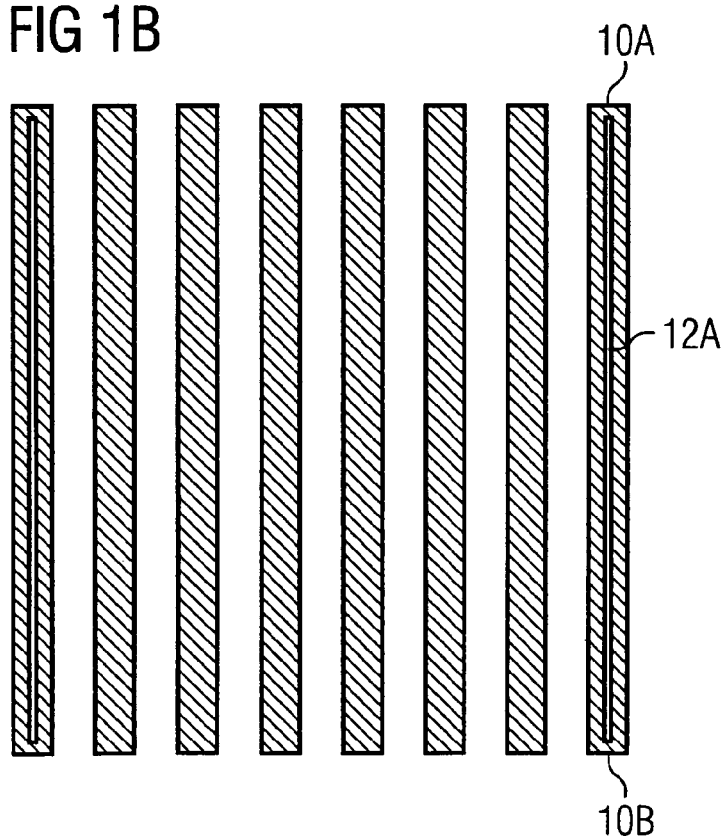
FIG. 1B shows a cross-sectional view of the device shown in FIG. 1A.

FIG. 1 highly schematically shows an embodiment of a device according to the invention, on the one hand in plan view (FIG. 1A) and on the other hand in cross section (FIG. 1B). Here, the device according to the invention has completely oxidized regions 11A which comprise a multiplicity of essentially square pores with $SiO_2$ pore walls. These regions 11A are enclosed by a frame 12 of walls with a silicon core 12A, which is open towards the surfaces 10A, 10B, with the silicon core merging into silicon dioxide over the cross section towards the outer side of the walls forming the frame.

Figure 2A:
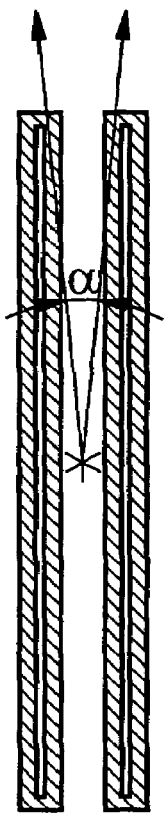
FIG. 2A shows the aperture angle α with which a luminescent volume can radiate into the space above (and below) the support material in a conventional pore which is fully surrounded by silicon walls.
Figure 2B:
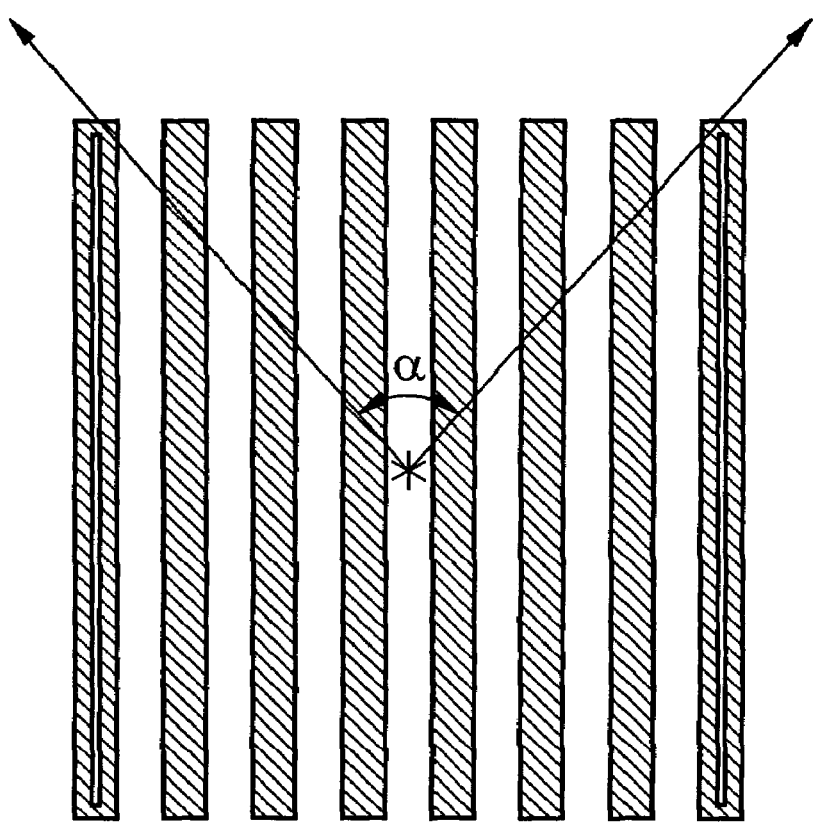
FIG. 2B shows the aperture angle α with which a luminescent volume can radiate into the space above (and below) the support material in a pore of a device according to the invention.

FIG. 2 shows the aperture angle α with which a luminescent volume or a luminescent surface of a pore of a device according to the invention (FIG. 2B) can radiate into the space above (and below) the substrate or support material, compared with the case in a conventional pore which is fully surrounded by silicon walls (FIG. 2A). In the device according to the invention, the aperture angle with which a luminescent volume or a luminescent surface in a pore can radiate into the space above (and below) the substrate is much greater than in a conventional pore which is fully surrounded by silicon walls. The smaller aspect ratio (aperture of oxidized region/length of pores) also decreases the required number of reflections which a ray experiences at a given angle before it reaches the opening of the pores. Compared with a porous silicon substrate without transparent regions, the device according to the invention provides a considerable improvement of the absolute signal yield in fluorescent and chemiluminescent analysis methods.

What is claimed is:

1. A device comprising:
a flat macroporous support material made of silicon and having surfaces;
a plurality of pores each having a diameter in a range of from 500 nm to 100 μm distributed over at least one surface region of the support material and extending from one surface through to the opposite surface of the support material;
at least one region having a plurality of with pore walls formed by a single layer and consisting substantially entirely of $SiO_2$; and
a frame of walls with a silicon core surrounding the at least one region and arranged essentially parallel to longitudinal axes of the pores and open towards the surfaces, wherein the silicon core merges into silicon dioxide over a cross section towards an outer side of the walls forming the frame.

2. The device according to claim 1, wherein the support material has a thickness between 100 to 5000 μm.

3. The device according to claim 1, wherein a pore density is in a range of from $1^4$ to $10^8/cm^2$.

4. The device according to claim 1, wherein the pores with $SiO_2$ pore walls are substantially square and the frame of walls with the silicon core is substantially square or rectangular in shape.

5. The device according to claim 1, wherein capture molecules selected from the group consisting of DNA, proteins, and ligands are covalently bound at least locally to at least one of the pores.

6. The device according to claim 5, wherein the capture molecules are oligonucleotide probes which are bound via terminal amino or thiol groups to linker molecules, which are in turn bound to the pores via covalent and/or ionic groups.

* * * * *

UNITED STATES PATENT AND TRADEMARK OFFICE
CERTIFICATE OF CORRECTION

| | | |
|---|---|---|
| PATENT NO. | : 7,410,794 B2 | |
| APPLICATION NO. | : 10/967090 | |
| DATED | : August 12, 2008 | |
| INVENTOR(S) | : Stephan Dertinger et al. | |

It is certified that error appears in the above-identified patent and that said Letters Patent is hereby corrected as shown below:

On the face of the patent:

At column 2, under OTHER PUBLICATIONS, "Foll,H." should read --Foll, H.--

At column 2, under Assistant Examiner, "Diramio" should read --DiRamio--

At column 2, under Abstract, line 7, "SiO2" should read --$SiO_2$--

In the Specifications:

At column 2, line 51, "nescence method)." should read --nescence method). When the substance to be detected, ….--

At column 2, line 55, "term "luminescence," is" should read --term "luminescence" is--

At column 2, line 63, ""luminescence,"" should read --"luminescence"--

At column 6, line 15, "increased pore spacing." should read --increased pore spacing. The regions with thin silicon walls….-- (paragraph space removed)

UNITED STATES PATENT AND TRADEMARK OFFICE
CERTIFICATE OF CORRECTION

PATENT NO. : 7,410,794 B2
APPLICATION NO. : 10/967090
DATED : August 12, 2008
INVENTOR(S) : Stephan Dertinger et al.

It is certified that error appears in the above-identified patent and that said Letters Patent is hereby corrected as shown below:

In the Claims:

At column 8, Claim 3, line 45, "$1^4$" should read --$10^4$--

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,410,794 B2
APPLICATION NO. : 10/967090
DATED : August 12, 2008
INVENTOR(S) : Stephan Dertinger et al.

Page 1 of 1

It is certified that error appears in the above-identified patent and that said Letters Patent is hereby corrected as shown below:

In the Claims:

At column 8, Claim 1, line 33, "having a plurality of with pore walls" should read --having a plurality of pores with pore walls--

Signed and Sealed this

Sixteenth Day of June, 2009

JOHN DOLL
*Acting Director of the United States Patent and Trademark Office*